United States Patent
Ellis et al.

(10) Patent No.: US 9,913,627 B2
(45) Date of Patent: Mar. 13, 2018

(54) SPECIMEN COLLECTION CONTAINER HAVING A FLUID SEPARATION CHAMBER

(71) Applicant: Becton, Dickinson and Company, Franklin Lakes, NJ (US)

(72) Inventors: Robert G. Ellis, Wayne, NJ (US); Keith A. Moskowitz, Monroe, NY (US); Craig A. Gelfand, Jackson, NJ (US); Raymond Wasek, Jamesburg, NJ (US); Bradley M. Wilkinson, North Haledon, NJ (US); Jean-Bernard Alla, Le Pont-de-Claix (FR); Kenneth Louis Lee, Denville, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 513 days.

(21) Appl. No.: 13/752,590

(22) Filed: Jan. 29, 2013

(65) Prior Publication Data
US 2014/0213934 A1    Jul. 31, 2014

(51) Int. Cl.
*A61B 5/00* (2006.01)
*A61B 10/00* (2006.01)

(52) U.S. Cl.
CPC ........ *A61B 10/007* (2013.01); *A61B 10/0096* (2013.01)

(58) Field of Classification Search
CPC . A61B 10/007; A61B 10/0045; A61B 5/1405; A61B 5/15003; A61B 5/150389; A61B 5/1427
USPC ................................................. 600/573, 575
See application file for complete search history.

(56) References Cited

U.S. PATENT DOCUMENTS

| | | | |
|---|---|---|---|
| 3,928,875 A | 12/1975 | Persson | |
| 4,106,497 A * | 8/1978 | Percarpio | 600/579 |
| 4,494,581 A | 1/1985 | Gordon | |
| 4,769,215 A | 9/1988 | Ehrenkranz | |
| 5,374,250 A * | 12/1994 | Dixon | 604/110 |
| 5,431,548 A * | 7/1995 | Koble, Jr. | F04D 29/106 |
| | | | 415/230 |

(Continued)

FOREIGN PATENT DOCUMENTS

| | | | |
|---|---|---|---|
| JP | 5664639 A | 6/1981 | |
| JP | 2003139780 A | 5/2003 | |

(Continued)

*Primary Examiner* — Daniel Cerioni
(74) *Attorney, Agent, or Firm* — The Webb Law Firm (57) ABSTRACT

A specimen collection container having a separation chamber includes a first chamber, a second chamber, and a valve located between the first chamber and the second chamber. In an open position, the valve permits fluid communication between the first chamber and the second chamber. In a closed position, the valve maintains fluid isolation between the first chamber and the second chamber. A fluid stream passes from the first chamber to the second chamber through the valve permitting a predetermined volume of fluid to pass from the first chamber to the second chamber. When the predetermined volume of fluid passes to the second chamber, the valve transitions from the open position to the closed position so that additional fluid of the fluid stream received by the first chamber is maintained in the first chamber in fluid isolation from the predetermined volume of fluid contained in the second chamber.

20 Claims, 8 Drawing Sheets

(56) References Cited

U.S. PATENT DOCUMENTS

| | | | |
|---|---|---|---|
| 6,939,312 B2 * | 9/2005 | Hodges | A61B 5/14514 600/583 |
| 7,674,434 B2 * | 3/2010 | Sakal et al. | 422/535 |
| 2002/0072702 A1 * | 6/2002 | Quay | 604/74 |
| 2003/0022392 A1 * | 1/2003 | Hudak | B01L 3/502 436/518 |
| 2005/0131361 A1 * | 6/2005 | Miskie | 604/350 |
| 2007/0270708 A1 * | 11/2007 | Hung | A61B 10/02 600/563 |
| 2009/0281485 A1 * | 11/2009 | Baker et al. | 604/35 |
| 2010/0137743 A1 * | 6/2010 | Nishtala et al. | 600/575 |
| 2011/0224610 A1 * | 9/2011 | Lum et al. | 604/125 |

FOREIGN PATENT DOCUMENTS

| | | |
|---|---|---|
| JP | 2011182907 A | 9/2011 |
| JP | 2012509489 A | 4/2012 |
| WO | 2004/026166 A2 | 4/2004 |

\* cited by examiner

SPECIMEN COLLECTION CONTAINER HAVING A FLUID SEPARATION CHAMBER

BACKGROUND OF THE INVENTION

Field of the Invention

The present invention is directed to a specimen collection container and, more particularly, a specimen collection container having two chambers separated by a valve for separating a patient's initially voided urine from the midstream portion of the urine sample.

Description of Related Art

When obtaining a urine sample for an ambulatory patient, it is generally preferable to collect the sample from the midstream portion of the urine stream. It is important to reject the "first-burst" urine from samples because the first volumes of voided urine carry a disproportionately higher level of bacteria. Bacteria is often picked up from external skin/tissue and also possibly from the urethral volume. The elevated bacteria level of the first stream or first-burst urine can lead to false-positive results for presence of bacteria, and could falsely suggest urinary tract infection, leading to unnecessary treatment or medication and inappropriate patient management. Since surface bacteria are always present, the chance for contamination of a urine sample is universal. As a result, urine samples are typically requested as "clean catch" or "mid-stream". Such requests require the patient or a care provider to use antiseptic wipes to disinfect external tissue. Additionally, patients are instructed to allow the first urine to fall into the toilet before filling a sample collection cup. It is believed that the first-burst urine not only contains elevated bacteria from the tissue surface, but in fact "washes" the external surfaces, such that there is little or no errant surface bacteria captured in later midstream urine volumes.

The state-of-the-art for midstream urine collection is essentially a manual process which relies entirely on the user or patient to perform the collection correctly. Typical instructions for midstream urine collection may require a user to void into the toilet, then stop urine flow, move the collection cup into position, void into the cup until it is full, stop the urine flow and move the filled cup away, and finish voiding into the toilet. Generally a user will be instructed to clean the surrounding external tissue/skin with an antiseptic wipe before voiding. The process is messy, with a user's hands being near the urine stream and often exposing the user's skin to urine.

Messiness and discomfort are not the only drawbacks from having a manual user-dependent process. In addition, patients need to be given adequate instructions placing an additional requirement and burden on both patient and caregiver. Often, such as in situations where privacy is impossible (e.g., in the midst of a busy emergency room setting), caregivers do not provide any instructions at all. In addition, patients may not understand or choose not to follow the instructions even when they are given, particularly if the patient is already nervous, scared, or agitated. For example, there is significant anecdotal evidence of people not using the antiseptic wipes, either because they burn or are uncomfortable or because patients mistake the antiseptic wipes for hand wipes to be used after providing the sample. Indeed, there is no way to know, short of actually watching the patient provide the urine sample, whether any of the instructions are actually followed.

There are also physiological complications that may contribute to elevated bacterial contamination. Some evidence indicates that intentionally interrupting the urine flow can lead to the reintroduction of bacteria, essentially creating a new "first-burst" of urine from the reinitiated urine flow. The reinitiated urine may not flow over the same skin/tissue as the first flow, and, as a result, may pick up bacteria from previously un-wetted skin. Another possibility is that the ceased urine flow may actually dislodge bacteria, dead cells, or other potential contaminants that would not have been available to contaminate urine during an otherwise normal voiding event. Thus, the manual start-stop-start again process for collecting midstream urine may itself contribute to some bacterial contamination.

The frequency of bacterial contamination of urine samples ranges from 10-40%, depending on the nature of the tests and the institution where the studies are performed. Such statistics indicate that the problem is widespread and quite common. It likely contributes to significant waste, both in increased cost and time associated with handling poor samples or running tests that give ambiguous or potentially useless data. Retesting may be appropriate in some circumstances; however, especially in outpatient settings, the patient may not be available to provide a second sample. Consequently, a re-test is either never performed or simply never requested.

Therefore, in view of the difficulties in obtaining a correct urine sample using currently available methods, there is a need for a collection apparatus which makes the collection process easier and reduces the risk of exposing the patient to the urine flow. The apparatus should be intuitive to use and should be designed to promote proper use and handling of the collected sample at all points before, during, and after voiding of urine. Further, the device should increase patient comfort and convenience by effectively selecting the midstream urine, so the user does not need to consciously force stop-then-start voiding. Not requiring the patient to start-stop-start voiding urine flow reduces the risk of natural physiologic contamination from stream interruption. Similarly, the device should require only minimal manipulation by a patient in order to collect the urine. Furthermore, the apparatus should eliminate the need for patients to be directly exposed to the urine stream. Finally, to ensure safe and easy transfer of the urine sample from the collection container to a specimen collection tube for testing, the device should include one or more access ports permitting direct flow of the collected sample from the container to a test tube.

SUMMARY OF THE INVENTION

Provided herein is a specimen collection container having a fluid separation chamber for receiving a fluid stream and for separating an initial volume of the fluid stream from a midstream portion of the fluid stream. The specimen collection container further includes a port for accessing and removing the midstream portion of the fluid from the container and for transferring the midstream portion to a sample collection tube. A method for collecting a fluid sample using a specimen collection container having a fluid separation chamber is also disclosed.

In accordance with one embodiment of the present invention, a specimen collection container includes a first chamber having an open top portion, a sidewall, and a bottom portion; a second chamber having a top, a closed bottom, and a sidewall; and a valve disposed between the first chamber and the second chamber. The valve is transitionable from an open position which permits fluid communication between the first chamber and the second chamber to a closed position which maintains fluid isolation between the first chamber and the second chamber. In the open position, a predetermined volume of fluid, received in the first chamber, may pass from the first chamber to the second chamber. When the predetermined volume of fluid passes to the second chamber, the valve transitions from the open position to the closed position such that additional fluid received within the first chamber is maintained in the first chamber in fluid isolation from the predetermined volume of fluid contained in the second chamber.

In certain configurations, the valve of the specimen collection container includes a channel extending between the first chamber and the second chamber and an absorbent expandable material. The absorbent expandable material absorbs the predetermined volume of fluid and expands to engage with the channel thereby transitioning the valve to the closed position. In certain alternative configurations, the container further comprises a gasket such that expansion of the absorbent expandable material positions the gasket to transition the valve. The absorbent expandable material may be a sponge.

In certain alternative configurations, the valve includes a channel, extending between the first chamber and the second chamber, and a buoyant float. When the second chamber receives the predetermined volume of fluid, the buoyant float engages the channel by a buoyancy force exerted on the float by the predetermined volume of fluid to transition the float from the open to the closed position. Optionally, a portion of the buoyant float initially seals the channel. Fluid passing from the first chamber to the second chamber disengages the float from the channel placing the valve in the temporarily open position.

In certain configurations, the specimen collection container further includes a port for accessing and removing a fluid sample from the first chamber. The port may include a nozzle defining a channel between the first chamber and an exterior of the specimen collection container; and a septum covering the channel which transitions from a closed position to an open position to allow removal of the fluid sample therefrom. The port may be disposed within the sidewall of the first chamber. The port may also include a needle having an external tip, an internal tip adjacent the first chamber, and a needle cannula extending therebetween, wherein fluid access to the first container is established through the needle cannula. Optionally, the external tip of the needle is recessed with respect to an external surface of the collection container for safe handling of the device.

In accordance with a further embodiment of the present invention, a specimen collection container includes an interior chamber having a bottom portion, a sidewall, and an open top; and an absorber disposed within the interior chamber which absorbs a predetermined volume of fluid. When a fluid stream enters the chamber through the open top, the absorber absorbs the predetermined volume. Additional fluid from the fluid stream is maintained in the internal chamber in fluid isolation from the fluid absorbed by the absorber. Optionally, the absorber includes bentonite, diatomaceous earth, pelites, zeolites, chitosan, alginates, starch-based powders, and/or sodium polyacrylate. The absorber may include a powder. Alternatively, the absorber may include a pouch enclosing an absorbent material.

In certain configurations, the interior chamber includes a screen separating the interior chamber into a first chamber and a second chamber with the absorber maintained therein. The screen permits fluid to pass from the first chamber to the second chamber but prevents the absorber from passing from the second chamber to the first chamber.

In accordance with a further embodiment of the present invention, a specimen collection container includes a first chamber having an open top portion, a sidewall, and a bottom portion; a second chamber having a top, a closed bottom, and a sidewall; and a valve disposed between the first chamber and the second chamber. The valve is transitionable from a first closed position in which the first chamber and the second chamber are in fluid isolation, to an open position which permits fluid communication between the first chamber and the second chamber, to a second closed position in which fluid isolation between the first chamber and the second chamber is restored. The valve may include a spring action flapper valve.

In certain configurations, a fluid entering the first chamber transitions the valve from the first closed position to the open position and the presence of a predetermined volume of fluid within the second chamber transitions the valve from the open position to the second closed position. Optionally, the valve includes a flapper valve transitionable from the first closed position to the open position when fluid contacts the surface of the flapper adjacent the first chamber. The valve is also subsequently transitionable from the open position to the second closed position when a predetermined volume of fluid received within the second chamber contacts the surface of the flapper adjacent the second chamber.

BRIEF DESCRIPTION OF THE DRAWINGS

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

DESCRIPTION OF THE PREFERRED EMBODIMENTS

For the purpose of facilitating understanding of the invention, the accompanying drawings and description illustrate preferred embodiments thereof, from which the invention, various embodiments of its structures, construction and method of operation, and many advantages may be understood and appreciated.

For purposes of the description hereinafter, the terms "upper", "lower", "right", "left", "vertical", "horizontal", "top", "bottom", "lateral" "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to FIGS. 1A-3B, a specimen collection container 10 includes a first chamber 12 in fluid communication with a second chamber 14 through a valve 16. The specimen collection container 10 is adapted to receive and separate a fluid stream into an initial or void volume and a midstream or sample volume. The midstream or sample volume can be removed from the specimen collection container 10 for biological testing. The container 10 is formed from any relatively inert medical grade polymer such as high density polyethylene or polystyrene. Alternatively, the container 10 may be formed from glass, paper or cellulose-based products.

Figure 3A:
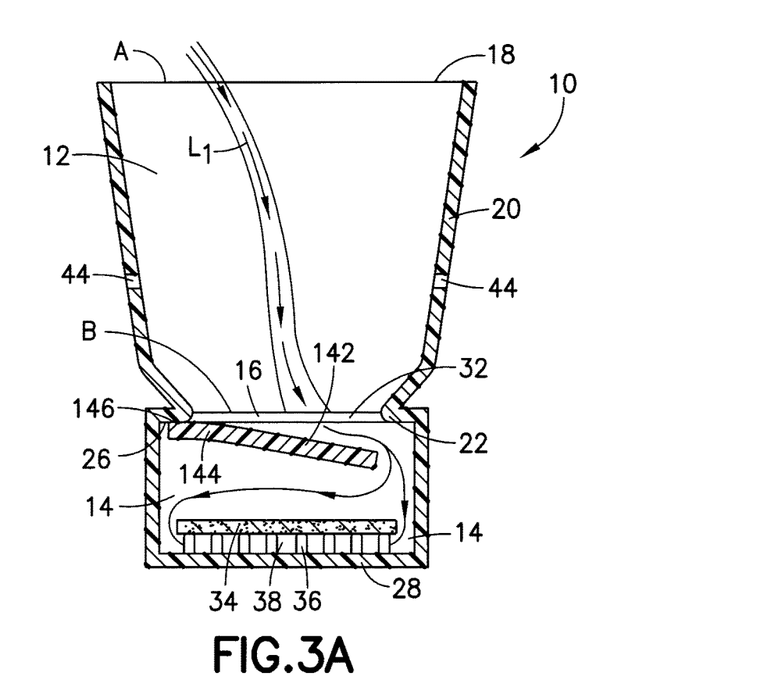
FIG. 3A is a cross-sectional front view of a specimen collection container with a valve in the open position in accordance with an embodiment of the present invention.
Figure 3B:
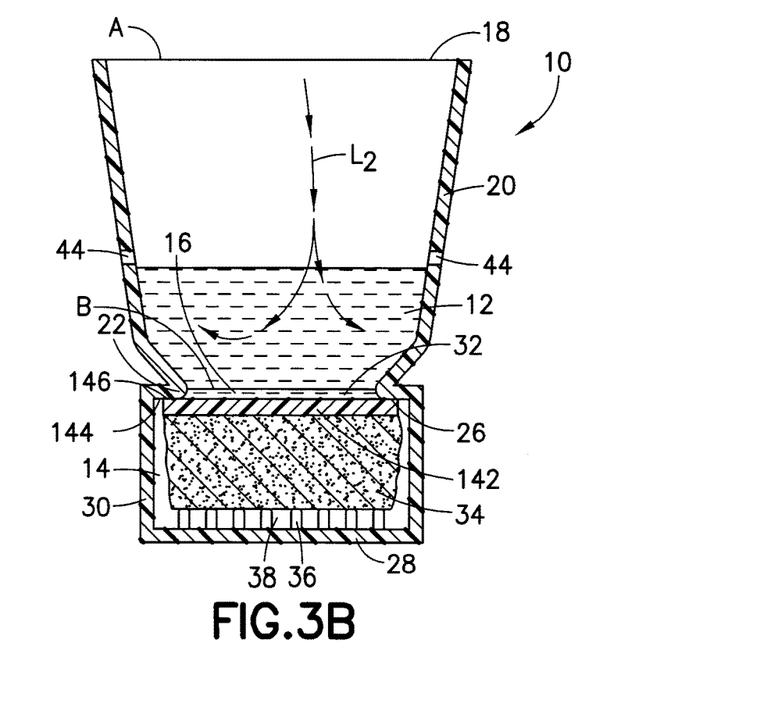
FIG. 3B is a cross-sectional front view of the container of FIG. 3A with the valve in the closed position in accordance with an embodiment of the present invention.

The specimen collection container 10 includes a first chamber 12 having an open top portion 18, a sidewall 20, and a closed bottom portion 22. As shown in FIGS. 3A-3B, the sidewall 20 may be sloped toward the bottom portion 22 of the first chamber 12 giving the first chamber 12 a funnel shape such that the diameter A of the open top portion 18 is larger than the diameter B of the closed bottom portion 22. In this configuration, fluid introduced to the funnel shaped chamber more easily slides downward towards the bottom of the container.

The first chamber 12 may include a fluid volume indicator 44 to show the amount of fluid contained therein. The first chamber 12 may be covered by a removable lid 24 which can be placed over the open top 18 of the first chamber 12 after the fluid sample is introduced to the chamber 12. The lid 24 prevents the fluid sample from leaking from the container 10 and prevents the sample from being contaminated.

The first chamber 12 is in fluid communication with the second chamber 14. The second chamber 14 includes a closed top 26, sidewall 20, and closed bottom 28. In one non-limiting embodiment, the second chamber 14 is positioned below the first chamber 12 such that the bottom portion 22 of the first chamber 12 also forms the closed top 26 of the second chamber 14. In one embodiment, the second chamber 14 has a volume of about 12 mL to 15 mL which may be smaller than the volume of the first chamber 12.

Fluid communication between the first chamber 12 and the second chamber 14 is established through the valve 16. The valve 16 transitions from a first position in which fluid communication between the first chamber 12 and second chamber 14 is established to a second position in which the first chamber 12 and the second chamber 14 are held in fluid isolation. In one embodiment, valve 16 includes a channel 32 that connects the first chamber 12 with the second chamber 14. When valve 16 is in the closed position, the channel 32 is blocked to prevent fluid in the first chamber 12 from flowing to the second chamber 14. Similarly, the valve 16 prevents fluid contained in the second chamber 14 from passing back to the first chamber 12. When the valve 16 is in the closed position, fluid follows fluid flow path $L_2$. In the open position, fluid flow $L_1$ is permitted between the first chamber 12 and the second chamber 14 through the channel 32.

Figure 1A:
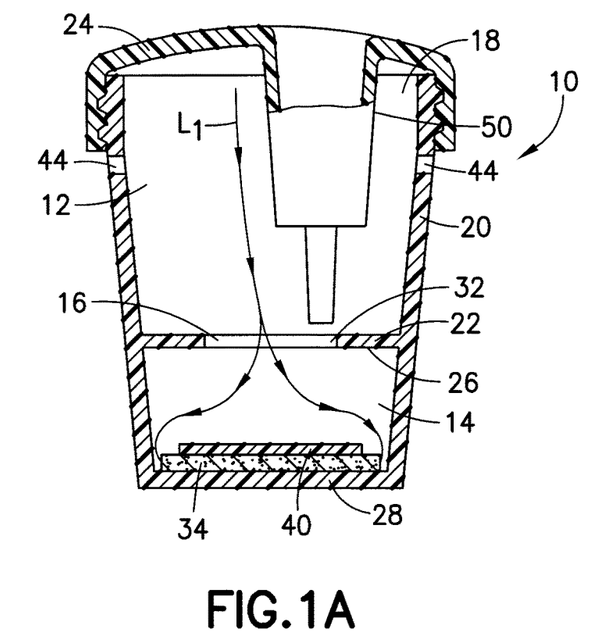
FIG. 1A is a cross-sectional front view of a specimen collection container with a valve in the open position in accordance with an embodiment of the present invention.
Figure 1B:
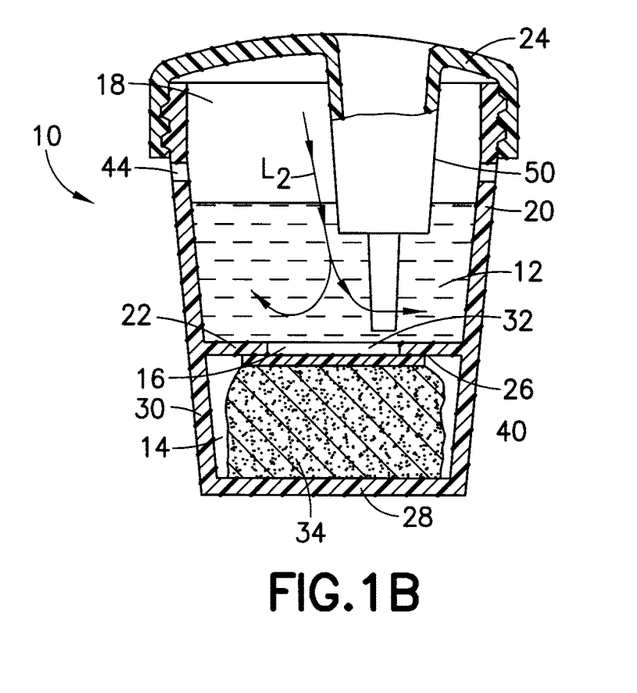
FIG. 1B is a cross-sectional front view of the container of FIG. 1A with the valve in the closed position in accordance with an embodiment of the present invention.

With reference to FIGS. 1A and 1B, in one non-limiting embodiment of the present invention, the valve 16 includes an expandable absorbent material 34, such as a compressed sponge, contained within the second chamber 14. The absorbent material 34 may be glued to the closed bottom 28 of the second chamber 14. In one exemplary embodiment, the absorbent material 34 has a diameter of 1.7 inches and an expanded height of about 5/8 inch. In comparison, the height of the second chamber 14 is about ½ inch. Consequently, when expanded, the absorbent material 34 takes up an entire volume of the second chamber 14. When wetted, the absorbent material 34 expands upward toward the closed top 26 to engage the channel 32. The absorbent material 34 may be formed in any configuration which allows for rapid fluid absorption and expansion in size. Some configurations increase the absorption rate by increasing the surface area of the absorbent material 34. With reference to FIGS. 11A-11E, possible shapes of the absorbent material 34 include, but are not limited to, a cylinder, a cylindrical shaped object with perforated holes, a cylindrical shape with wedges removed, a donut shape, and a plurality of separate thinner cylinders.

With reference again to FIGS. 3A and 3B, according to one non-limiting embodiment, the second chamber 14 includes a ribbed base 36. The absorbent material 34 is placed on the ribbed base 36 or similar support structure. The support structure elevates the absorbent material 34 permitting fluid to collect in the space 38 beneath the absorbent material 34 and allowing the fluid to be absorbed by a bottom surface of the absorbent material 34. Exposing an additional surface of the absorbent material 34 to fluid increases the absorption rate.

According to a further non-limiting embodiment, the valve 16 further includes a gasket 40 for creating a watertight seal in the channel 32, as shown in FIGS. 1A-1B. The gasket 40 is attached to a top portion of the absorbent material 34. The gasket 40 can be, for example, a polymeric foam disk. It is noted that the gasket 40 effectively blocks a portion of the absorbent material 34 from absorbing liquid. Accordingly, it is important that other surfaces of the absorbent material 34 are accessible to fluid flow $L_1$ so that the absorbent material 34 expands as quickly as possible. As the wetted absorbent material 34 expands and rises in an upward direction, the gasket 40 engages the channel 32, thereby sealing the channel 32 and, effectively, transitioning the valve 16 to the closed position. Once the gasket 40 is in place and engaged with the channel 32, the first chamber 12 and the second chamber 14 are in fluid isolation from one another. Accordingly, any additional fluid that enters the first chamber 12 through the open top 18 is maintained in the first chamber 12. This fluid maintained in the first chamber 12 is the midstream urine sample.

In a further non-limiting embodiment, the valve 16 consists of a buoyant float 142 which is forced in an upward direction toward the channel 32 as the fluid level of the second chamber 14 rises. In one embodiment, the buoyant float 142 includes gasket 40 for forming a seal between the float 142 and channel 32.

Figure 2A:
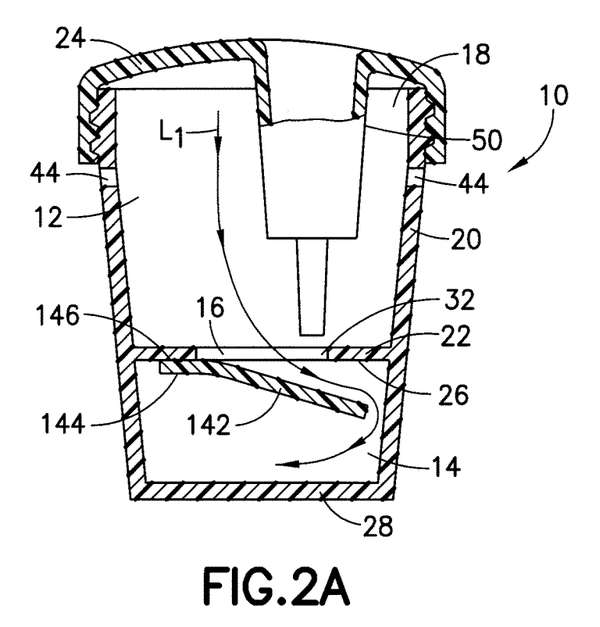
FIG. 2A is a cross-sectional front view of a specimen collection container with a valve in the open position in accordance with an embodiment of the present invention.
Figure 2B:
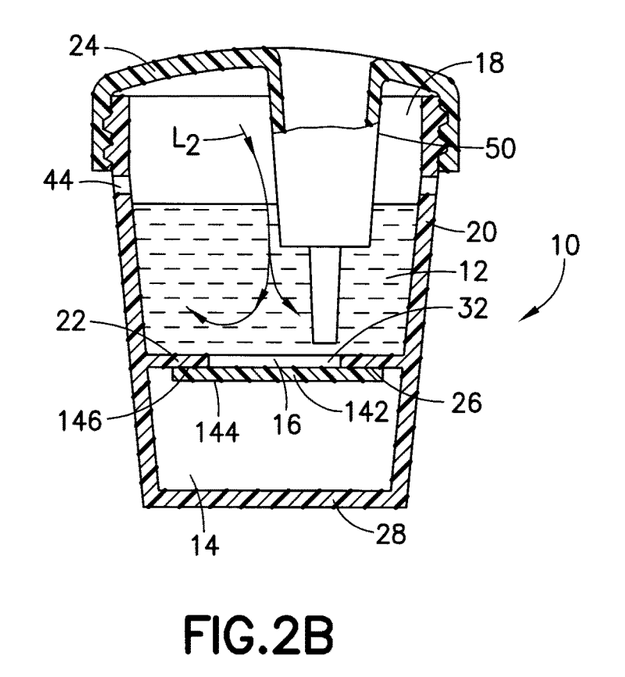
FIG. 2B is a cross-sectional front view of the container of FIG. 2A with the valve in the closed position in accordance with an embodiment of the present invention.

With reference to FIGS. 2A and 2B, in a further embodiment of the invention, the valve 16 is a "flapper valve". In the flapper valve, a portion 144 of the float 142 is attached to the closed top 26 of the second chamber 14 forming a hinge 146. In one embodiment, the hinge 146 is a living hinge. In another embodiment, the flapper valve includes a mechanical spring. The float 142 is held in close proximity to the channel 32 such that, initially, the float 142 covers the channel 32. Force exerted on the float 142 from fluid flow $L_1$ entering the first chamber 12 pushes the float 142 away from the channel 32 allowing fluid to pass directly through the channel 32 from the first chamber 12 to the second chamber 14. As the fluid level of the second chamber 14 increases, the range of movement for the float 142 is reduced, until, ultimately, the float 142 is held in place against the top 26 of the second chamber 14 and the channel 32. Once the float 142 is in place against the channel 32, fluid flow $L_2$ from the first chamber 12 to the second chamber 14 is blocked. Therefore, additional fluid introduced to the first chamber 12 is collected and maintained in the first chamber 12. The fluid collected within the first chamber 12 is the midstream portion of the urine stream.

With reference again to FIGS. 3A and 3B, the valve 16 of the specimen collection container 10 may also include both a float 142 and expandable absorbent material 34. When wetted, the absorbent material 34 increases in size eventually contacting the float 142 of the flapper valve 16 and forcing the float 142 toward the channel 32 to form a seal. When expanded, the absorbent material 34 maintains the float 142 in the closed position, thereby ensuring that the first chamber 12 and the second chamber 14 remain in fluid isolation even when the specimen container is jostled or moved.

Figure 4:
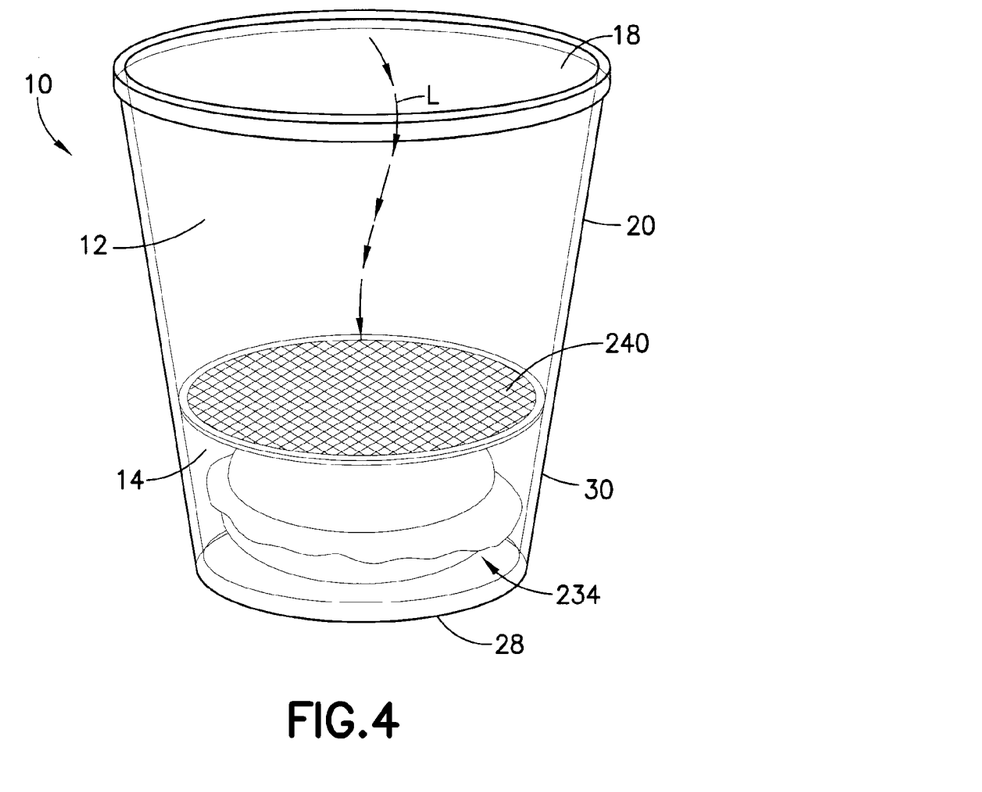
FIG. 4 is a perspective view of a specimen collection container having an absorbent pouch in accordance with an embodiment of the present invention.
Figure 5:
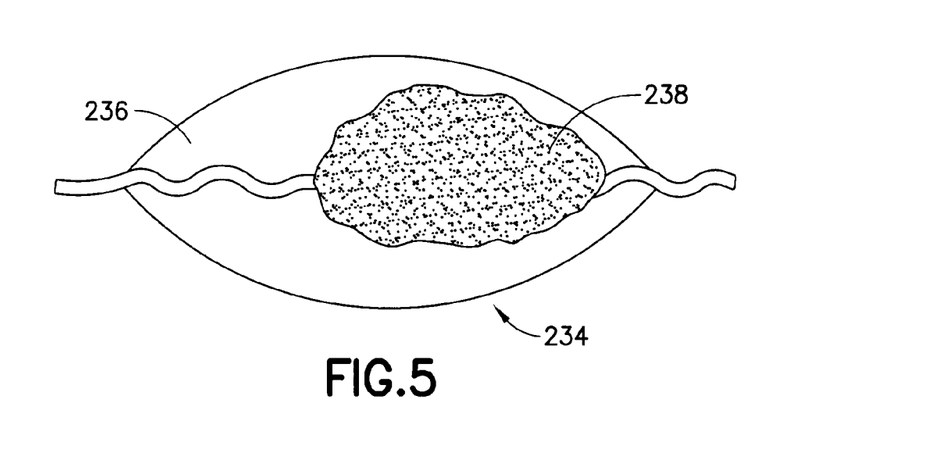
FIG. 5 is a perspective view of the absorbent pouch of FIG. 4, in accordance with an embodiment of the present invention, with a partial cut-away portion to reveal the interior of the pouch.

With reference to FIGS. 4 and 5, according to a further embodiment of the present invention, an absorbent pouch 234 is included within the sample collection container 10. The pouch 234 may be a non-woven filter paper bag 236 enclosing a micro-absorbent powder 238. Fluid enters the container according to fluid flow L. The pouch 234 absorbs a first predetermined volume of the fluid. The absorbed portion corresponds with the initial burst or voided urine which is held in isolation in the second chamber in the embodiments of the invention described above. In the present embodiment, once the pouch 234 reaches a saturation point, indicating that it has absorbed the predetermined amount of fluid, any additional fluid introduced to the container 10 is maintained in the container 10 in liquid form.

In one embodiment, the container 10 includes a screen 240 separating the first chamber 12 from the second chamber 14. The screen 240 effectively holds the pouch 234 within the second chamber 14 and prevents the pouch from floating toward the top of the container as the fluid level increases. The screen 240 could be formed from a wire mesh or from a disk having a plurality of perforated holes.

Figure 6:
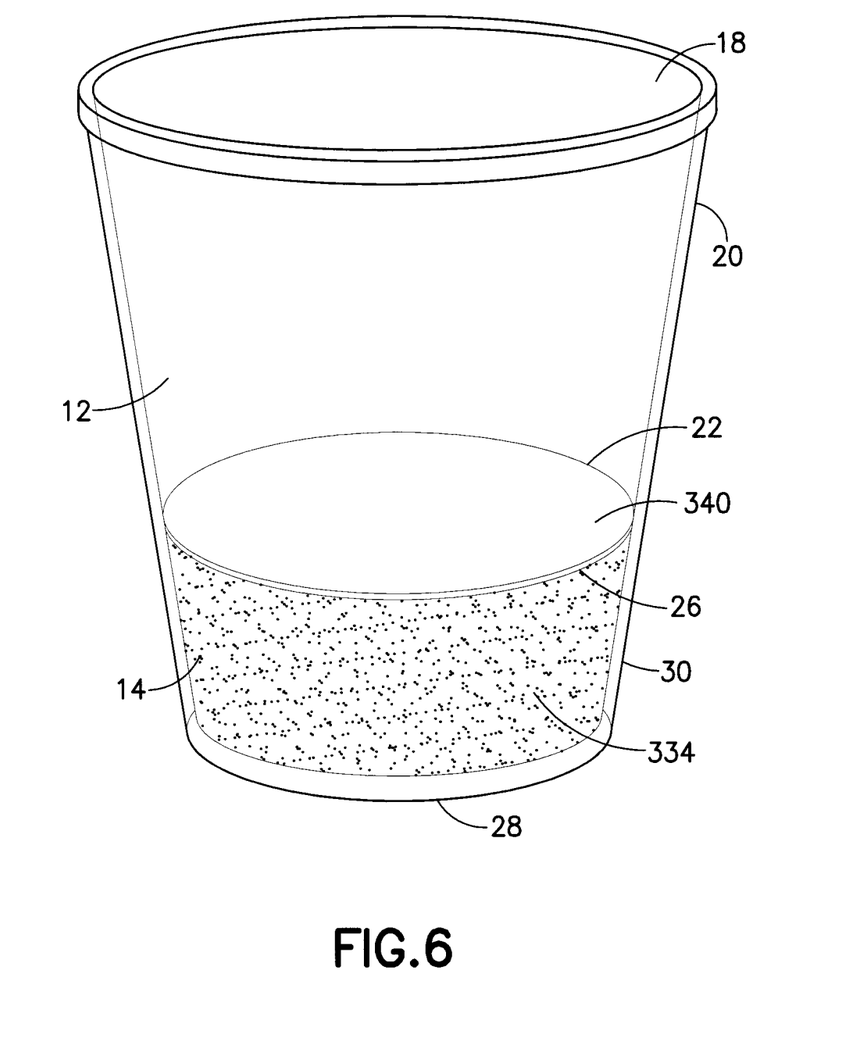
FIG. 6 is a perspective view of a specimen collection container having an absorbent material in accordance with an embodiment of the present invention.

With reference to FIG. 6, according to a further embodiment of the present invention, the first chamber 12 and the second chamber 14 are separated by a piece of filter paper 340. The second chamber 14 contains an absorbent powder 334. The absorbent powder 334 may be a mineral based compound or a synthetic compound. Examples of mineral based absorbent compounds include bentonite and diatomaceous earth. Bentonite is an absorbent aluminum phyllosilicate formed from impure clay. Diatomaceous earth is a compound composed of absorbent silica particles. Other natural absorbent materials include: pelites, zeolites, and chitosan. Organic absorbent powders are commercially available from a number of sources including: Sigma-Aldrich, LLC, MedTrade Products Ltd., and Haliburton. Absorbent alginates or starch based powders can also be used within the scope of the invention. Most synthetic absorbent powders are formed from sodium polyacrylate. One commercially available sodium polyacrylate powder is "Insta-Snow" produced by Steve Spangler, Inc. of Englewood, Colo.

When wetted, the absorbent powder forms a solid structure which will not pass through the filter paper 340, thereby separating the first chamber 12 from the second chamber 14. The powder 334 holds a predetermined initial volume of fluid. Once the powder 334 is saturated, any additional fluid introduced to the container 10 is maintained in the container 10 in liquid form. As with previous embodiments described above, the unabsorbed liquid portion constitutes the midstream urine sample. Alternatively, fiber papers are known in the art which are impregnated with sodium polyacrylate particles. Absorbent paper of this type is made by Safetec of America, Inc. located in Buffalo, N.Y. One or more pieces of the absorbent paper are placed in the second chamber 14 of the container 10. The absorbent paper is used to absorb a first-burst of fluid in much the same way as the absorbent powder.

Figure 7:
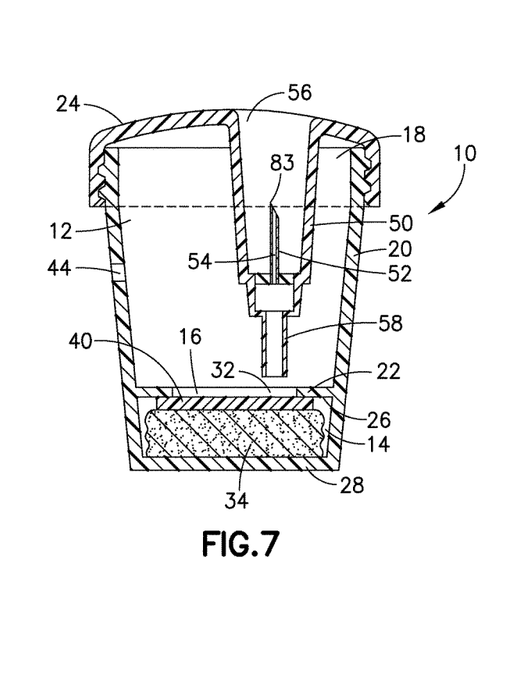
FIG. 7 is a cross-sectional front view of a specimen collection container, having an outflow port, in accordance with an embodiment of the present invention.

With reference to FIG. 7, according to one non-limiting embodiment, the invention further includes an outflow port 50 for removing the sample (e.g., the midstream urine) from the sample container 10. In one embodiment, the outflow port 50 comprises a needle 52 having a needle cannula 59 for accessing the sample contained in the first chamber 12. The needle 52 may be located in a cut-away portion 56 of the sidewall 20 or lid 24 such that a proximal end 83 of the needle 52 is recessed from the surfaces of the container 10. The needle 52 is in contact with an access tube 58 that extends into the first chamber 12 of the container 10. Fluid passes through access tube 58 before entering the needle cannula 54 for removal from the container 10.

Figure 10:
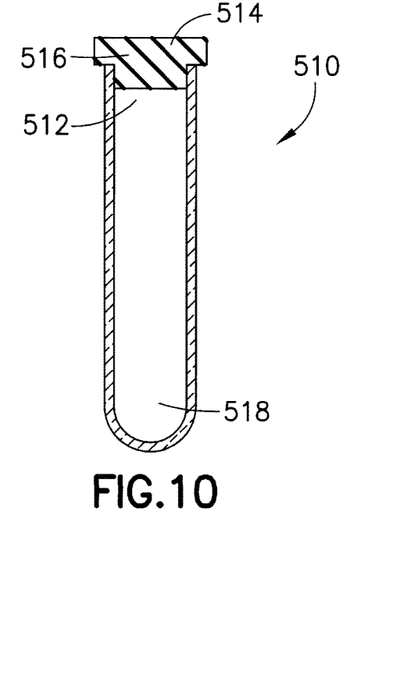
FIG. 10 is a cross-sectional front view of a sample collection tube, in accordance with an embodiment of the present invention.
Figure 11A:
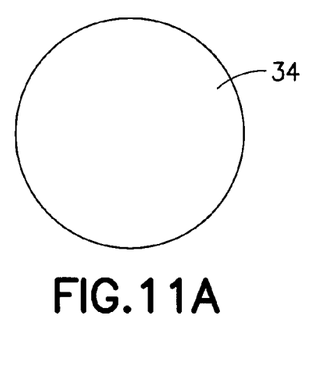
FIG. 11A is a top view of an absorbent material for use in a specimen collection container, in accordance with an embodiment of the present invention.
Figure 11B:
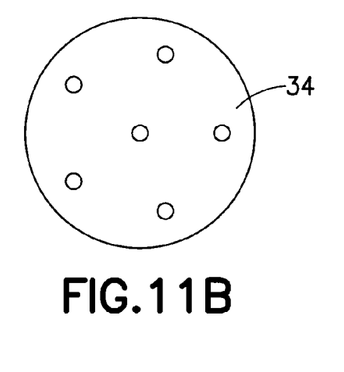
FIG. 11B is a top view of an absorbent material for use in a specimen collection container, in accordance with an embodiment of the present invention.
Figure 11C:
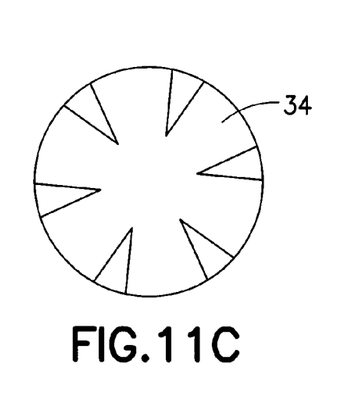
FIG. 11C is a top view of an absorbent material for use in a specimen collection container, in accordance with an embodiment of the present invention.
Figure 11D:
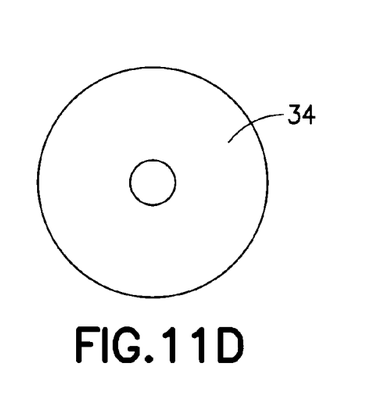
FIG. 11D is a top view of an absorbent material for use in a specimen collection container, in accordance with an embodiment of the present invention.
Figure 11E:
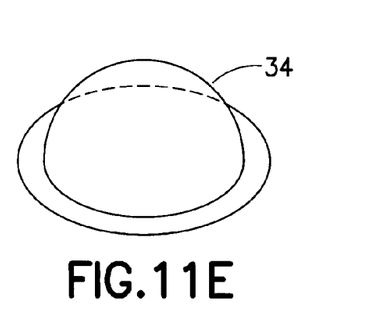
FIG. 11E is a perspective view of an absorbent material for use in a specimen collection container, in accordance with an embodiment of the present invention.

With reference to FIGS. 7 and 10, to extract a sample from the container 10, a user places a sample collection tube 510

(e.g., a test tube) over the needle 52. Generally, the tube 510 includes an open end 512 covered by a stopper 514 having a pierceable septum 516. The needle 52 pierces the septum 516 accessing an interior portion 518 of the tube 510 and creating a fluid connection between the first chamber 12 and the tube 510 through the needle cannula 54. In one configuration, the sample collection tube 510 may be evacuated such that upon engagement with the container 10, fluid is drawn from the container interior into the sample collection tube 510 by vacuum draw. In another configuration, the entire container assembly may be inverted allowing fluid (e.g., the midstream urine sample) to flow from the collection container 10 to the specimen collection tube 510.

Figure 8:
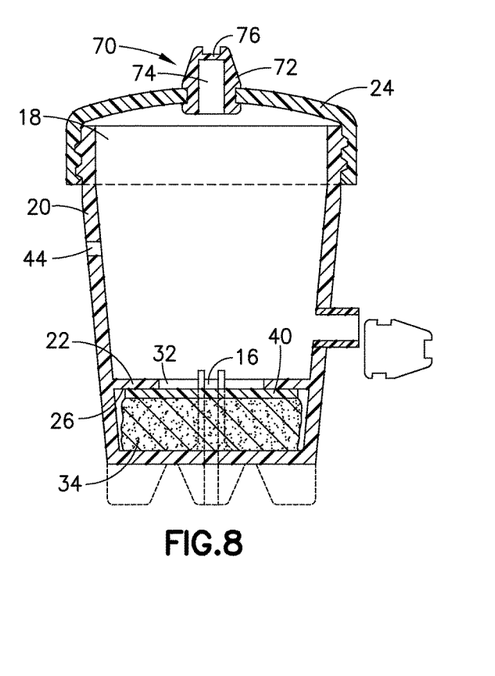
FIG. 8 is a cross-sectional front view of a specimen collection container, in accordance with an embodiment of the present invention, having a sharps-free elastomeric port.
Figure 9:
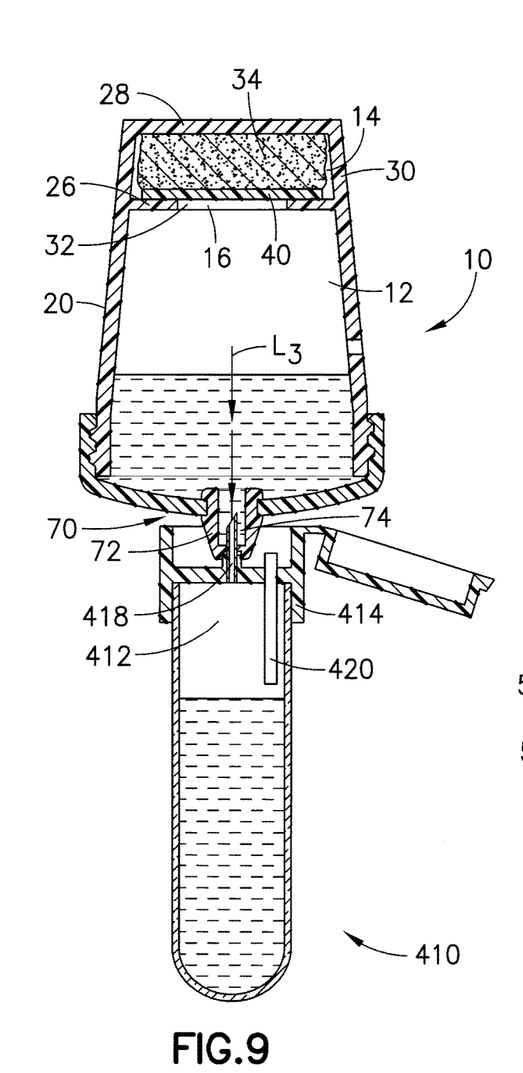
FIG. 9 is a cross-sectional front view of the specimen collection container of FIG. 8 engaged with a sample collection tube for removing a sample from the container, in accordance with an embodiment of the present invention.

With reference to FIG. 8, according to an alternative embodiment, a sharps free port 70 extends from either the sidewall 20 or lid 24 of the first chamber 12. The sharps free port 70 includes a nozzle 72 extending from the container 10 or lid 24. A channel 74 is defined through the nozzle 72 allowing access to the first chamber 12. An elastomeric seal 76 covers the channel 74 preventing fluid from leaking from the port 70 until a user is prepared to collect the fluid in a specimen collection tube 410, as shown in FIG. 9. With reference to FIG. 9, the specimen collection tube 410 has an open top 412 covered by a stopper or flip-cap closure 414. The flip-cap closure 414 includes an access tube 418. The access tube 418 fits within the channel 74 of the nozzle 72 and pushes the elastomeric seal 76 out of the way to establish a fluid connection between the first chamber 12 and the sample collection tube 410. Once the fluid connection is established, the container 10 is inverted allowing the fluid sample to flow, along flow path L₃, from the first chamber 12 to the collection tube 410 by gravity. The flip-cap closure 414 may further include a vent 420 allowing air displaced by the fluid sample to escape from the enclosed tube 410.

The presently claimed sample collection container 10 is used to collect a sample of midstream urine for testing. In use, a patient directs a urine stream to the container 10 through the open top 18 of the first chamber 12. The urine stream flows down the sidewall 20 toward the channel 32 and valve 16. In one embodiment, the first chamber 12 is funnel shaped having a sloped sidewall 20. The sloped sidewall 20 allows fluid to more easily flow downward toward the bottom 22 of the first chamber 12. The funnel shaped first chamber 12 also ensures that all of the first-burst or first urine stream will pass through the first chamber 12 and enter the second chamber 14. For containers having straight sides and right angled corners, a portion of the first-burst may pool in the first chamber 12, potentially contaminating the fluid sample.

The fluid stream passes through the channel 32 and valve 16 and collects in the second chamber 14. As the fluid level in the second chamber 14 increases to a pre-determined level, the valve 16 transitions from an open to a closed position. The pre-determined volume for the second chamber 14 may be between about 12 mL and 15 mL. The valve 16 should not transition to the closed position until the pre-determined volume of fluid passes to the second chamber 14. If the valve 16 closes too soon, a portion of the initial burst of urine will be trapped in the first chamber 12 contaminating the midstream urine sample. If the valve 16 closes too slowly, some of the first-burst urine, which initially passed to the second chamber 14, will flow back to the first chamber 12 contaminating the urine sample contained in the first chamber 12.

Once the required amount of midstream urine is collected in the first chamber 12, the specimen collection container 10 is removed from the urine stream. Alternatively, the patient may consciously stop urine flow to prevent overflowing the container 10. The container 10 may include a fluid level indicator line 44 to inform the patient when the necessary amount of fluid has been collected. The lid 24 is then placed over the open top 18 of the first chamber 12 to prevent fluid from leaking from the container 10 or from being contaminated. The midstream urine sample is then removed from the first chamber 12 through the outflow port 50 or from the sharps free port 70 using any of the extraction procedures described above.

What is claimed is:

1. A specimen collection container comprising:
    a first chamber configured to maintain a fluid, the first chamber having an open top portion, a sidewall, and a bottom portion;
    a second chamber having a top, a closed bottom, and a sidewall;
    a valve disposed between the first chamber and the second chamber, the valve adjacent the top of the second chamber and the bottom portion of the first chamber and transitionable from an open position which permits fluid communication between the first chamber and the second chamber to a closed position which maintains fluid isolation between the first chamber and the second chamber;
    an expandable material disposed within the second chamber, the expandable material being expandable to transition the valve from the open position to the closed position; and
    a port having a closed position and an open position, wherein the port is configured to provide access to a fluid sample of the fluid from the first chamber via the port when the port is in the open position; and
    wherein the fluid is maintained in the first chamber when the valve is in the closed position and the port is in the closed position and the fluid is inaccessible from the first chamber via the port or via the valve when the valve is in the closed position and the port is in the closed position.

2. The specimen collection container of claim 1, wherein the valve comprises:
    a channel extending between the first chamber and the second chamber; and
    wherein the expandable material is capable of absorbing a predetermined volume of fluid and expanding to engage with the channel thereby transitioning the valve to the closed position.

3. The specimen collection container of claim 1, further comprising a gasket such that expansion of the expandable material positions the gasket to transition the valve.

4. The specimen collection container of claim 1, wherein the expandable material is a sponge.

5. The specimen collection container of claim 2, wherein the valve comprises:
    a float which engages the channel when the valve is transitioned from the open position to the closed position.

6. The specimen collection container of claim 5, wherein a portion of the float initially seals the channel, and wherein fluid passing from the first chamber to the second chamber disengages the float from the channel placing the valve in the open position.

7. The specimen collection container of claim 1, wherein the port comprises:
    a nozzle defining a channel between the first chamber and an exterior of the specimen collection container; and a septum covering the channel which transitions the port from the closed position to the open position to allow removal of the fluid sample from the first chamber.

8. The specimen collection container of claim 1, wherein the port is disposed within the sidewall of the first chamber.

9. The specimen collection container of claim 1, wherein the port is disposed within a removable lid adapted to cover the open top portion of the first chamber.

10. The specimen collection container of claim 1, wherein the port comprises a needle having an external tip, an internal tip adjacent the first chamber, and a needle cannula extending between the external tip and the internal tip, wherein fluid access to the first chamber is established through the needle cannula.

11. The specimen collection container of claim 10, wherein the external tip of the needle is recessed with respect to an external surface of the collection container.

12. The specimen collection container of claim 1, wherein the expandable material is glued to the closed bottom of the second chamber.

13. The specimen collection container of claim 2, wherein upon absorption of the predetermined volume of fluid, the expandable material has an expanded height, and wherein when the expandable material is at the expanded height, the expandable material acts on the valve.

14. The specimen collection container of claim 13, wherein the second chamber has a predetermined volume and wherein upon absorption of the predetermined volume of fluid, the expandable material fills the predetermined volume of the second chamber.

15. A specimen collection container comprising:
a first chamber configured to maintain a fluid, the first chamber having an open top portion, a sidewall, and a bottom portion;
a second chamber having a predetermined volume and having a top, a closed bottom, and a sidewall;
a valve disposed between the first chamber and the second chamber, the valve adjacent the top of the second chamber and the bottom portion of the first chamber and transitionable from an open position which permits fluid communication between the first chamber and the second chamber to a closed position which maintains fluid isolation between the first chamber and the second chamber;
an expandable material expandable upon receipt of a predetermined volume of fluid to transition the valve from the open position to the closed position, wherein upon absorption of the predetermined volume of fluid, the expandable material fills the second chamber; and
a port having a closed position and an open position, wherein the port is configured to provide access to a fluid sample of the fluid from the first chamber via the port when the port is in the open position; and
wherein the fluid is maintained in the first chamber when the valve is in the closed position and the port is in the closed position and the fluid is inaccessible from the first chamber via the port or via the valve when the valve is in the closed position and the port is in the closed position.

16. The specimen collection container of claim 15, wherein upon absorption of the predetermined volume of fluid, the expandable material has an expanded height, and wherein when the expandable material is at the expanded height, the expandable material acts on the valve.

17. The specimen collection container of claim 15, wherein the valve comprises:
a channel extending between the first chamber and the second chamber; and
a gasket located within the second chamber,
wherein the expandable material absorbs the predetermined volume of fluid and expands to cause the gasket to engage with the channel thereby transitioning the valve to the closed position.

18. A specimen collection container comprising:
a first chamber configured to maintain a fluid, the first chamber having an open top portion, a sidewall, and a bottom portion;
a second chamber having a top, a closed bottom, and a sidewall;
a valve disposed between the first chamber and the second chamber, the valve adjacent the top of the second chamber and the bottom portion of the first chamber and transitionable from an open position which permits fluid communication between the first chamber and the second chamber to a closed position which maintains fluid isolation between the first chamber and the second chamber;
a gasket associated with the second chamber, said gasket configured to cooperate with the top of the second chamber upon receipt of a predetermined volume of fluid in the second chamber to transition the valve from the open position to the closed position such that additional fluid received within the first chamber is maintained in the first chamber in fluid isolation from the predetermined volume of fluid contained in the second chamber; and
a port having a closed position and an open position, wherein the port is configured to provide access to a fluid sample of the fluid from the first chamber via the port when the port is in the open position; and
wherein the fluid is maintained in the first chamber when the valve is in the closed position and the port is in the closed position and the fluid is inaccessible from the first chamber via the port or via the valve when the valve is in the closed position and the port is in the closed position.

19. The specimen collection container of claim 18, wherein the gasket is associated with an expandable material, said expandable material being formed from an absorbent material configured to absorb the predetermined volume of fluid and expand causing the gasket to transition the valve from the open position to the closed position.

20. The specimen collection container of claim 18, wherein a volume of the second chamber is smaller than a volume of the first chamber.

* * * * *